(12) United States Patent
Kolb et al.

(10) Patent No.: US 7,466,235 B1
(45) Date of Patent: Dec. 16, 2008

(54) WIRELESS DEVICE WITH EMERGENCY MEDICAL AND RELATED INFORMATION

(76) Inventors: Kenneth Allen Kolb, 7520 E. Sunnyvale Dr., Scottsdale, AZ (US) 85258; Lynn Susan Kolb, 7520 E. Sunnyvale Dr., Scottsdale, AZ (US) 85258

( * ) Notice: Subject to any disclaimer, the term of this patent is extended or adjusted under 35 U.S.C. 154(b) by 146 days.

(21) Appl. No.: 11/323,440

(22) Filed: Dec. 30, 2005

(51) Int. Cl.
- G08B 23/00 (2006.01)
- H04Q 7/00 (2006.01)
- H04M 11/04 (2006.01)

(52) U.S. Cl. .............................. 340/573.1; 340/539.11; 340/539.12; 340/539.25; 455/404.1; 348/14.03

(58) Field of Classification Search .............. 340/573.1, 340/539.11; 455/404.1; 348/14.03
See application file for complete search history.

(56) References Cited

U.S. PATENT DOCUMENTS

2002/0170954 A1* 11/2002 Zingher et al. .............. 235/375
2003/0141977 A1* 7/2003 Brown et al. ................ 340/574
2004/0266390 A1 12/2004 Faucher et al.
2005/0221796 A1* 10/2005 Pellegrino et al. ........... 455/410
2006/0142057 A1* 6/2006 Schuler et al. ........... 455/556.1

OTHER PUBLICATIONS

Arizona Republic article: 3 Letters to Save Life? Easy Call Article dated Sep. 23, 2005.
Reproduced Article: "ICE—In Case of Emergency", Dec. 30, 2005.

* cited by examiner

*Primary Examiner*—Donnie L Crosland
(74) *Attorney, Agent, or Firm*—Gregory J. Nelson

(57) ABSTRACT

A wireless communication device provided with an Emergency Identification system actuated by a dedicated EI button. In emergency situations, a third party such as a first responder may quickly access limited medical and personal information concerning the incapacitated individual by depressing the EI button and scrolling through the EI system screens. The device may be incorporated into a variety of wireless devices such as cellular phones, PDA's, Blackberry's® and other devices. While the information made available is carefully selected so as to not enable identity theft, a lock-out or disabling feature is included.

9 Claims, 2 Drawing Sheets

WIRELESS DEVICE WITH EMERGENCY MEDICAL AND RELATED INFORMATION

The present invention relates to wireless devices and more particularly to a device such as a mobile phone, PDA or other wireless communication device commonly used by an individual which device is provided with an emergency feature having an emergency key which, when activated, will display limited information concerning an individual to enable emergency personnel to initiate medical treatment and take other action such as contacting the individual's primary physician (s) and other emergency contacts.

FIELD OF THE INVENTION

In some emergencies such as automobile wrecks and strokes, the individual is incapacitated so severely that the individual is unable to communicate with responding emergency personnel. The inability to communicate limits the treatment and response that medical and other attendants can provide as first responders. For example, medical personnel not having information about the individual's medical conditions, allergies, blood type and other considerations must limit initial first response treatment. Since the initial proper treatment is often critical to survival, a device that would provide, at least, limited information concerning the incapacitated patient would be extremely beneficial.

BACKGROUND OF THE INVENTION

There are various devices in the prior art which attempt to deal with critical situations as described above. Some of the simplest devices consist of a medical ID bracelet which an individual wears which may display certain, limited information such as allergies and blood types which will assist medical personnel. However, often these devices are not updated with current information and are of limited value.

Patent Publication 2004/0266390 discloses a device for calling an emergency number in response to an activation signal. The device is a wearable, portable emergency device that initiates communication with a mobile phone and supplies the information from a non-volatile memory in response to prompts from a 911 operator. In the case of a patient who cannot speak, the operator can examine the stored information to use it assist in the decision as to what emergency personnel to send. The disadvantage of this system is that it requires interaction with an operator.

Another approach is the ICE or in case of an emergency program which was started in the United Kingdom. The program allows the cell and/or mobile phone user to designate several ICE numbers and allows first responders to an accident to notify or contact individuals at the designated ICE numbers such as family. This system requires the person designated as an ICE number be aware of the designation and the designee must be able to confirm certain personal information concerning the cell and/or mobile phone user such as name, birth date and medical information. While the ICE system is achieving some acceptance, the system requires that the cell phone has to be operable and, further, that the ICE contact individuals are available.

BRIEF SUMMARY OF THE INVENTION

Briefly, the present invention may be used in connection with a digital device such as a mobile cell phone, PDA, Palm Pilot®, Blackberry® or other wireless, digital communication device. The device is equipped with an emergency feature having an additional button, termed the "EI" or emergency information button, strategically placed and, preferably, identified in a manner so as to be easily distinguished from other buttons on the keypad of the device. The EI system can be activated in the event of a medical emergency. When the EI button is depressed, a color image of the owner/subscriber appears on the display screen for purposes of identification by physical comparison with the individual. Additional information such as the individual's name, age, physical description and significant medical information is displayed. The medical information set forth includes items such as blood type, allergies and any underlining condition such as diabetes or other conditions that may effect treatment. The attendant can scroll through the display and additional information including the name and telephone of one or more physicians and emergency contact names and telephone numbers are listed. The device is primarily intended for use when the subscriber is injured or otherwise incapacitated and is unable to communicate with emergency personnel.

In any medical emergency such as a car accident, plane crash or heart attack, time is of the essence. The addition of the EI button to the keypad of the wireless device enables first responders such as paramedics, police, fire or other personnel to immediately obtain emergency information when the device is located, either found on or near the individual. This will assist emergency medical and other personnel to identify the individual using the electronic image and identification data. In addition, significant medical history, contact information, and the name or names of the primary physicians are also provided. Other personal information such as social security numbers and addresses which are unnecessary for emergency action which might enable a finder of the device to steal the subscriber's identity is not available.

BRIEF DESCRIPTION OF THE DRAWINGS

The above and other advantages and objects of the present invention will become more apparent from the following description, claims and drawings in which:

DETAILED DESCRIPTION OF THE DRAWINGS

Figure 1:
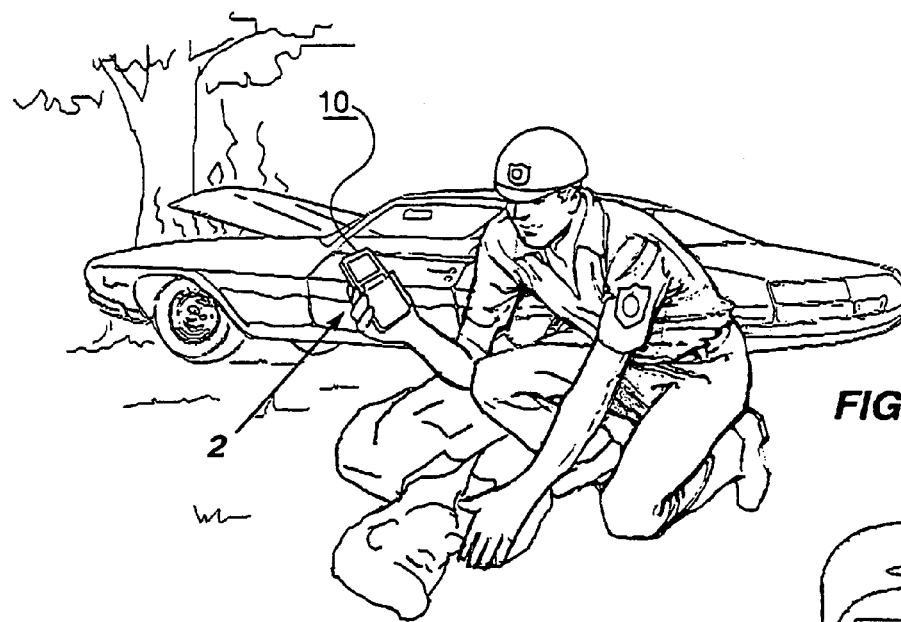
FIG. 1 illustrates a representative accident site with emergency medical assistance arriving at the accident scene and attending to the injured, unconscious individual.
Figure 2:
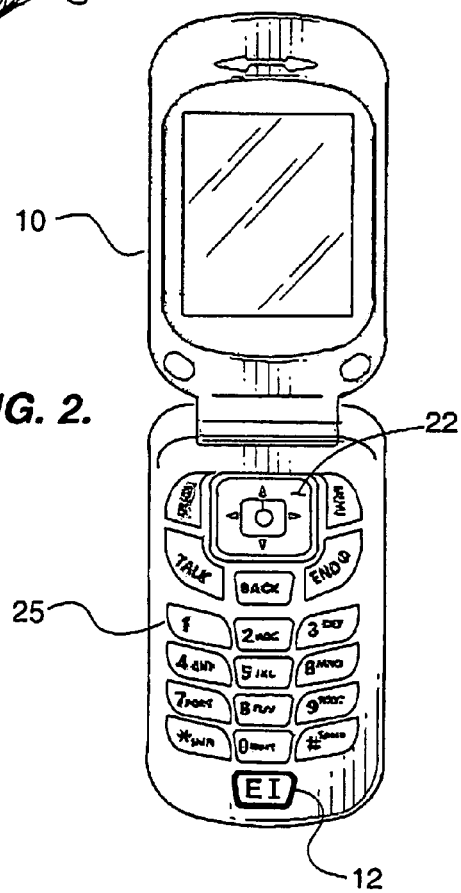
FIG. 2 is a front view of a device, in this case a cellular telephone equipped with the EI system.
Figure 3:
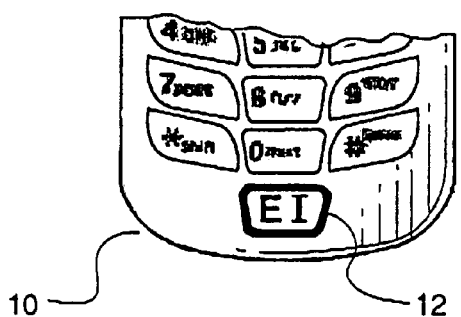
FIG. 3 is a large view of a portion of the keypad of the individual's cellular telephone showing the location of the emergency information button.

Turning now to the drawings, the present invention provides a wireless device 10, as described above, with an additional function termed an "Emergency Identification Feature." The emergency identification feature is actuated by a separate, dedicated button 12 designated the "EI" button which is located in a convenient location, preferably at a central location below the conventional keypad, as seen in FIGS. 2 and 3. The EI button 12 is prominently marked by indicia such as letters 'EI' and may be provided in a distinctive color or outline and, as shown, is a slightly trapezoidal button peripherally outlined with the letters 'EI' prominently appearing on the button. Actuation of the EI button will cause a series of displays to be made available to the user. Preferably the device 10 is a cellular phone, PDA, smart phone or other wireless device into which is incorporated a digital camera. Thus, the owner of the device will initially input certain information which can be accessed in an emergency situation as shown in FIG. 1. The information is input using the keypad 25. Preferably, the series of screens will display information as shown in FIGS. 4 through 7.

The device 10 includes a cell phone which may be analog or digital and will include a circuit board, an antenna, a screen such as an LCD, a keypad 25, a microphone, a speaker and a power source such as a battery. Typically, ROM and flash memory chips provide storage for the operating system of features of the cellular device. An RF power section handles power management and RF amplifier handles signals. These features and components are common to cellular phones and, as discussed, may be incorporated as part of a multi-functional wireless device. The EI system utilizes the existing cellular phone technology and information can be input, stored and displayed using the existing components.

Figure 4:
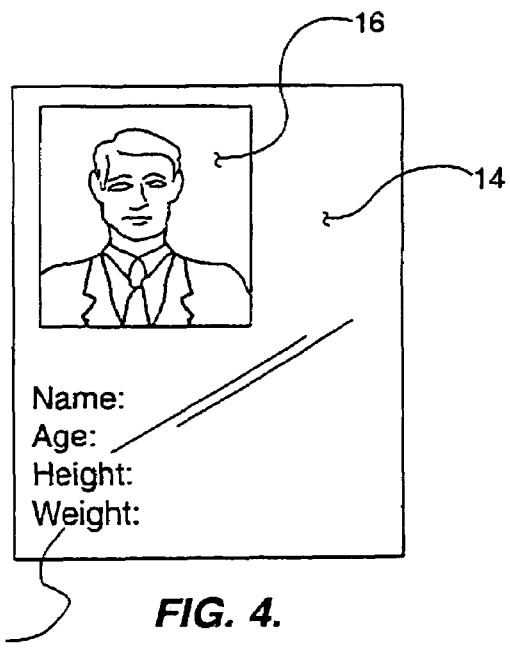
FIG. 4 shows a display screen which initially displays an image of the subscriber and certain, limited personal information.
Figure 5:
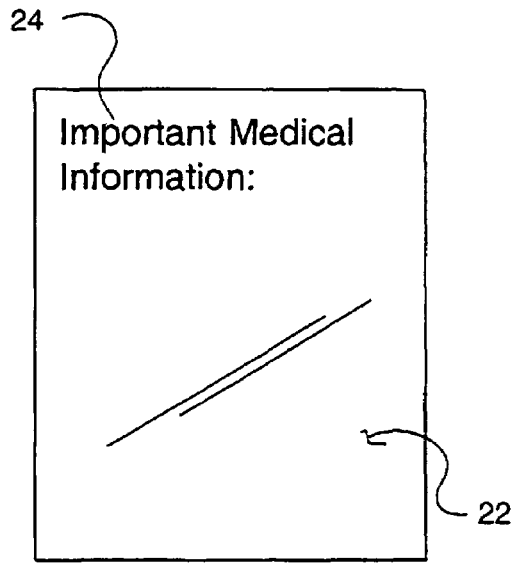
FIG. 5 shows a subsequent screen which is accessed by scrolling which screen displays certain important medical information.
Figure 6:
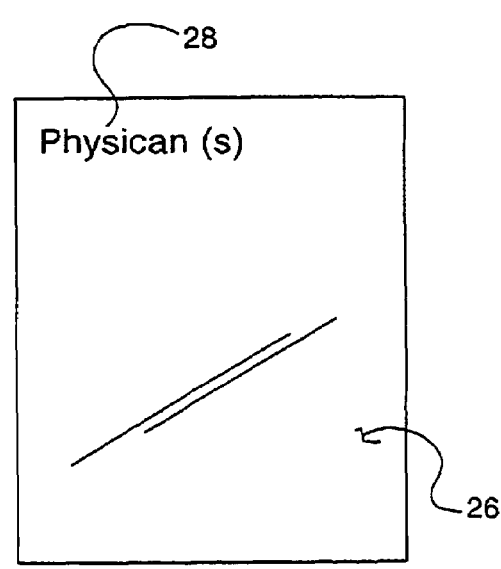
FIG. 6 is a screen which may be accessed by scrolling which lists the names one or more of the subscriber's physicians.
Figure 7:
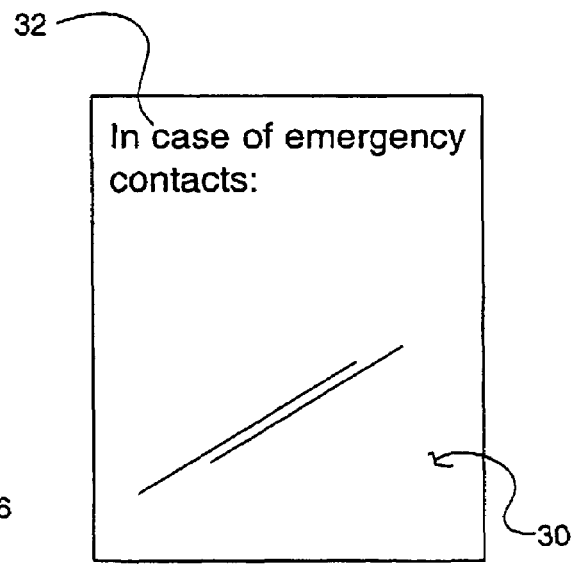
FIG. 7 is a screen setting forth information regarding persons to be contacted in the case of an emergency.

In FIG. 4, the information initially displayed on the first screen 14 when the EI button is depressed includes the image 16 of the owner. The image is stored in the device and is a digital photograph taken of the user using the digital camera technology in the device. The digital image is stored in the memory section of the device. Personnel such as a paramedic or law enforcement officer can compare the photographic image 16 with that of an unconscious, comatose individual who is incommunicado. This will enable the responder to confirm that the individual being assisted is, in fact, the individual to which the personal information applies.

In addition, the initial screen 14 will provide additional information 18 such as the name and other physical description pertaining to the individual such as age, height and weight. Additional information can be provided on a subsequent screen 22 which are accessed by using the scroll button 20. Important medical information screen may include information such as blood type, medical conditions such as diabetes or drug allergies listed at 24.

An additional screen 26 may be accessed which will display additional information such as the name and telephone of the one or more primary physicians 28. Finally, emergency contact information 32 such as names of family members, relatives and appropriate telephone numbers may be accessed on screen 30. It will be apparent that the information may be displayed on any number of screens as convenient in accordance with the data, screen size and character size.

FIG. 1 depicts a typical situation in which emergency identification system would be utilized. In a medical emergency such as a car accident, plane crash, terrorist attack, heart attack and the like, time is critical. The emergency information button 12 added to a device 10, such as a cellular telephone, enables first responders such as paramedics, police, fire department or other emergency personnel to obtain important emergency information immediately when the cellular telephone is located on or near an injured individual. The responder R will quickly identify the individual I and confirm the identity of the injured individual by comparing the digital image 16 and identification data 18. Additional information such as medical history 24, names of physicians 28 and emergency contact information 32 is then made available as the responder R scrolls.

An important feature is the information entered into the EI system is carefully selected to enable first responders to attend to the individual. However, the information will not include other personal information of the type which would facilitate identity theft in the event the device is lost. The various items of information must be entered by the subscriber by initially using the digital camera which is incorporated in the device. Other information must be keyed in using the keypad 25, similar to text messaging. The information is customized for the particular subscriber and is not in the form of a check list.

A further feature of the present invention is a security feature in the event a telephone is lost or misplaced. While the information displayed by using the EI system can be accessed by a third party other than the subscriber, the type of information is limited so as to protect against identity theft. Furthermore, the emergency system includes a lock-out device. The lock-out device can be accessed by calling the number assigned to the subscriber and then entering a code such as a personal identification number or PIN. The entry of the code will cause the information otherwise available through use of the EI system to be either entirely erased or locked-out so that it cannot be accessed by unauthorized individuals.

In the event the device 10 is left unattended by the subscriber, provision is made to prevent third parties from altering or removing the image and information that have been stored in the memory of the device. When the subscriber initially programs the device with the emergency information, as discussed above, the user will be prompted to enter a password such as a personal identification number or PIN at the same time. While the information which has been entered can be accessed without entering any code or PIN, any modification of the information will require entry of a code or PIN. This will protect the subscriber from unauthorized alteration of the emergency information.

Accordingly, the EI system of the present invention can be made available in connection with various devices such as cell phones and other wireless devices and may be used in the event of an emergency situation to provide vital information to attending emergency personnel.

It will be obvious to those skilled in the art to make various changes, alterations and modifications to the invention described herein. To the extent such changes, alterations and modifications do not depart from the spirit and scope of the appended claims, they are intended to be encompassed therein.

We claim:
1. An emergency information system comprising:
 (a) a wireless communication device including a circuit board with digital camera technology, memory, display and keypad permitting the owner to input selected personal and medical information into the memory for display and a digital photograph of the owner to be taken, stored and updated; and
 (b) an emergency information button which when actuated immediately presents on the display selected medical information and limited personal information sufficient only for identification purposes along with the digital photo identifying the owner.

2. The emergency information system of claim 1 wherein the button is a dedicated button located adjacent the keypad.

3. The emergency information system of claim 1 wherein the selected information includes emergency contact information.

4. The emergency information system of claim 2 wherein the button is prominently identified by the letters EI.

5. The emergency information system of claim 1 wherein the device is selected from the group consisting of cellular phones, PDA's, Blackberrys®, Palm Pilots® and smart phones.

6. The emergency information system of claim 1 wherein programming information into the memory is protected by a password.

7. The emergency information system of claim 6 wherein the password is a PIN.

8. An emergency information system comprising:
   (a) a wireless communication device including a circuit board with memory, display and keypad, said keypad permitting the owner to input selected personal and medical information into the memory for display;
   (b) an emergency information button which when actuated immediately presents on the display selected personal and medical information sufficient for identification purposes including a digital photo identifying the owner; and
   (c) further including a security feature which may be remotely activated preventing unauthorized access to the information.

9. The emergency information system of claim 8 wherein the security feature is remotely activated by telephoning the device and entering a security code.

* * * * *